(12) United States Patent
Gupta et al.

(10) Patent No.: US 10,737,060 B2
(45) Date of Patent: Aug. 11, 2020

(54) CATHETER HUBS

(71) Applicant: BOSTON SCIENTIFIC SCIMED, INC., Maple Grove, MN (US)

(72) Inventors: Ajay Gupta, Shoreview, MN (US); David Raab, Minneapolis, MN (US); Mark S. Smith, Coon Rapids, MN (US); Ken Fredrikson, Howard Lake, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 30 days.

(21) Appl. No.: 15/704,928

(22) Filed: Sep. 14, 2017

(65) Prior Publication Data
US 2018/0071485 A1   Mar. 15, 2018

Related U.S. Application Data

(60) Provisional application No. 62/394,506, filed on Sep. 14, 2016.

(51) Int. Cl.
*A61M 25/00* (2006.01)
*A61M 25/01* (2006.01)

(52) U.S. Cl.
CPC ........ *A61M 25/0097* (2013.01); *A61M 25/01* (2013.01); *A61M 2025/0004* (2013.01); *A61M 2025/0175* (2013.01); *A61M 2205/58* (2013.01)

(58) Field of Classification Search
CPC .. A61M 25/01; A61M 25/10; A61M 25/0097; A61M 2020/0004; A61M 2020/0175; A61M 2205/58
See application file for complete search history.

(56) References Cited

U.S. PATENT DOCUMENTS

| | | | |
|---|---|---|---|
| 3,680,562 A | * | 8/1972 | Wittes .................. A61M 25/02 604/500 |
| 4,027,668 A | | 6/1977 | Dunn |
| 4,068,660 A | | 1/1978 | Beck |
| 4,838,873 A | | 6/1989 | Landskron et al. |
| 5,113,900 A | * | 5/1992 | Gilbert .................. F16K 15/063 137/515.5 |
| 5,224,939 A | * | 7/1993 | Holman ................ A61M 5/158 604/528 |

(Continued)

FOREIGN PATENT DOCUMENTS

| DE | 3049612 A1 | 7/1982 |
|---|---|---|
| EP | 2926857 A1 | 10/2015 |

(Continued)

OTHER PUBLICATIONS

International Search Report and Written Opinion dated Dec. 8, 2017 for International Application No. PCT/US2017/051613.

*Primary Examiner* — Jason E Flick
*Assistant Examiner* — Mark A Igel
(74) *Attorney, Agent, or Firm* — Seager, Tufte & Wickhem, LLP (57) ABSTRACT

A hub assembly for connection to a medical device having a built in strain relief. The hub assembly may comprise a hub body having a proximal end and a distal end. A lumen may extend from the proximal end to the distal end of the hub body. The distal end of the hub body may have a rounded surface. The rounded surface may have a radius of curvature of greater than 1 millimeter.

18 Claims, 6 Drawing Sheets

(56) References Cited

U.S. PATENT DOCUMENTS

| | | | |
|---|---|---|---|
| 5,879,333 A * | 3/1999 | Smith | A61M 25/0014 604/164.04 |
| 5,899,891 A * | 5/1999 | Racz | A61M 25/0017 604/264 |
| 5,997,562 A * | 12/1999 | Zadno-Azizi | A61M 25/0662 604/158 |
| 6,068,622 A | 5/2000 | Sater et al. | |
| 6,117,108 A | 9/2000 | Woehr et al. | |
| 6,283,950 B1 * | 9/2001 | Appling | A61M 25/0075 600/585 |
| 6,287,278 B1 | 9/2001 | Woehr et al. | |
| 6,616,630 B1 | 9/2003 | Woehr et al. | |
| 6,971,390 B1 * | 12/2005 | Vasek | A61M 25/0097 285/245 |
| 7,494,478 B2 | 2/2009 | Itou et al. | |
| 7,625,360 B2 | 12/2009 | Woehr et al. | |
| 7,972,313 B2 | 7/2011 | Woehr et al. | |
| 8,568,372 B2 | 10/2013 | Woehr et al. | |
| 8,979,802 B2 | 3/2015 | Woehr | |
| 8,986,283 B2 | 3/2015 | Rajendran et al. | |
| 2002/0128631 A1 * | 9/2002 | Hayman | A61J 1/2096 604/525 |
| 2003/0195471 A1 | 10/2003 | Woehr et al. | |
| 2005/0203485 A1 * | 9/2005 | Lee | A61M 25/0097 604/523 |
| 2005/0209581 A1 | 9/2005 | Butts et al. | |
| 2006/0052750 A1 | 3/2006 | Lenker et al. | |
| 2006/0116638 A1 | 6/2006 | Woehr et al. | |
| 2006/0212023 A1 * | 9/2006 | Cross | A61M 25/0097 604/523 |
| 2007/0005001 A1 * | 1/2007 | Rowe | A61M 25/0014 604/19 |
| 2007/0233047 A1 * | 10/2007 | Kerr | A61M 25/0014 605/539 |
| 2008/0294145 A1 * | 11/2008 | Eddings | A61M 25/0014 604/533 |
| 2009/0192496 A1 * | 7/2009 | Suwito | A61M 25/0097 604/533 |
| 2009/0292273 A1 * | 11/2009 | Racz | A61M 25/0097 604/533 |
| 2010/0191193 A1 | 7/2010 | Pajunk et al. | |
| 2010/0312193 A1 * | 12/2010 | Stratton | A61M 39/02 604/175 |
| 2011/0065368 A1 * | 3/2011 | Sather | B24B 37/32 451/385 |
| 2011/0190734 A1 | 8/2011 | Graffam et al. | |
| 2013/0053781 A1 | 2/2013 | Woehr et al. | |
| 2014/0088516 A1 * | 3/2014 | Stevenson | A61M 5/00 604/263 |
| 2014/0155745 A1 * | 6/2014 | Duncan | A61M 25/0097 600/435 |
| 2014/0316327 A1 | 10/2014 | Rajendran et al. | |
| 2014/0316328 A1 | 10/2014 | Rajendran et al. | |
| 2015/0026806 A1 | 1/2015 | Kawaguchi | |
| 2016/0008581 A1 | 1/2016 | Ang et al. | |

FOREIGN PATENT DOCUMENTS

| | | |
|---|---|---|
| JP | 2011510744 A | 4/2011 |
| JP | 2013022255 A | 2/2013 |
| JP | 2014128341 A | 7/2014 |
| WO | 03015638 A2 | 2/2003 |
| WO | 2013056223 A1 | 4/2013 |
| WO | 2013062504 A1 | 5/2013 |
| WO | 2014140257 A1 | 9/2014 |
| WO | 2015104336 A1 | 7/2015 |
| WO | 2017074673 A1 | 5/2017 |

* cited by examiner

CATHETER HUBS

CROSS REFERENCE TO RELATED APPLICATIONS

This application claims the benefit of provisional U.S. Patent Application No. 62/394,506, filed on Sep. 14, 2016, which is hereby incorporated by reference in its entirety.

TECHNOLOGY FIELD

The present application relates generally to a hub, and in particular, to a microcatheter hub.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

This disclosure provides design, material, manufacturing methods, and use alternatives for medical devices.

In a first example, a hub assembly for connection to a medical device may comprise a hub body having a proximal end and a distal end and a lumen extending from the proximal end to the distal end of the hub body. The distal end of the hub body may have a rounded surface having a radius of curvature of greater than 1 millimeter.

Alternatively or additionally to any of the examples above, in another example, the hub assembly may further comprise at least one gripping portion formed in a side surface of the hub body.

Alternatively or additionally to any of the examples above, in another example, the at least one gripping portion may comprise a generally flat region.

Alternatively or additionally to any of the examples above, in another example, the rounded surface of the distal end may gradually transition to the generally flat region.

Alternatively or additionally to any of the examples above, in another example, the at least one gripping portion may comprise two gripping portions, each positioned on an opposing side of the hub body.

Alternatively or additionally to any of the examples above, in another example, a distal region of the lumen may comprise a flared region that increases in diameter from a first location at least proximate the proximal end of the hub body to a second location at least proximate the distal end of the hub body Alternatively or additionally to any of the examples above, in another example, the lumen may have a step-wise change in diameter at the first location.

Alternatively or additionally to any of the examples above, in another example, the rounded surface may extend into the lumen.

Alternatively or additionally to any of the examples above, in another example, a proximal region of the lumen may comprise a tapered region that is configured to direct a fluid distally from a larger diameter to a smaller diameter region.

Alternatively or additionally to any of the examples above, in another example, the distal end of the hub body may comprise a Luer connection.

Alternatively or additionally to any of the examples above, in another example, a radius of curvature of the rounded surface may be greater than 2 millimeters.

Alternatively or additionally to any of the examples above, in another example, a radius of curvature of the rounded surface may be greater than 3 millimeters.

Alternatively or additionally to any of the examples above, in another example, the hub assembly may be configured to be affixed to a proximal end of a microcatheter.

Alternatively or additionally to any of the examples above, in another example, the hub body may comprise a polycarbonate.

Alternatively or additionally to any of the examples above, in another example, the hub body may be transparent.

In another example, a hub assembly for connection to a medical device may comprise a hub body having a proximal end and a distal end and a lumen extending from the proximal end to the distal end of the hub body. The distal end of the hub body may have a rounded surface, the rounded surface having a radius of curvature of greater than 3 millimeters.

Alternatively or additionally to any of the examples above, in another example, the hub assembly may further comprise at least one gripping portion formed in a side surface of the hub body.

Alternatively or additionally to any of the examples above, in another example, the at least one gripping portion may comprise a generally flat region.

Alternatively or additionally to any of the examples above, in another example, the rounded surface of the distal end may gradually transition to the generally flat region.

Alternatively or additionally to any of the examples above, in another example, the at least one gripping portion may comprise two gripping portions, each positioned on an opposing side of the hub body.

Alternatively or additionally to any of the examples above, in another example, a distal region of the lumen may comprise a flared region that increases in diameter from a first location at least proximate the proximal end of the hub body to a second location at least proximate the distal end of the hub body.

Alternatively or additionally to any of the examples above, in another example, the lumen may have a step-wise change in diameter at the first location.

Alternatively or additionally to any of the examples above, in another example, the rounded surface may extend into the lumen.

Alternatively or additionally to any of the examples above, in another example, a proximal region of the lumen may comprise a tapered region that is configured to direct a fluid distally from a larger diameter to a smaller diameter region.

Alternatively or additionally to any of the examples above, in another example, the hub body may comprise a polycarbonate.

Alternatively or additionally to any of the examples above, in another example, the hub body may be transparent.

In another example, a hub assembly for connection to a medical device may comprise a generally tubular hub body increasing in diameter from a proximal end and a distal end thereof, a lumen extending from the proximal end to the distal end of the hub body, and at least one gripping portion formed on a first side surface of the generally tubular hub body. The distal end of the hub body may have a rounded surface having a radius of curvature of greater than 1 millimeter.

Alternatively or additionally to any of the examples above, in another example, the at least one gripping portion may comprise a generally flat region.

Alternatively or additionally to any of the examples above, in another example, the rounded surface of the distal end may gradually transition to the generally flat region.

Alternatively or additionally to any of the examples above, in another example, a distal region of the lumen may comprise a flared region that increases in diameter from a first location at least proximate the proximal end of the hub body to a second location at least proximate the distal end of the hub body.

Alternatively or additionally to any of the examples above, in another example, the rounded surface may extend into the lumen.

In another example, a microcatheter may comprise an elongate shaft having a proximal end, a distal end, and a lumen extending therebetween and a hub assembly affixed to the proximal end of the elongate shaft. The hub assembly may comprise a generally tubular hub body increasing in diameter from a proximal end and a distal end thereof, a lumen extending from the proximal end to the distal end of the hub body, and at least one gripping portion formed on a first side surface of the generally tubular hub body. The distal end of the hub body may have a rounded surface having a radius of curvature of greater than 1 millimeter.

Alternatively or additionally to any of the examples above, in another example, the hub assembly may be molded over the proximal end of the elongate shaft.

Alternatively or additionally to any of the examples above, in another example, the proximal end of the elongate shaft may be press fit into the lumen of the hub assembly.

Alternatively or additionally to any of the examples above, in another example, the proximal end of the elongate shaft may be secured within the lumen of the hub assembly with an adhesive.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Figure 1:
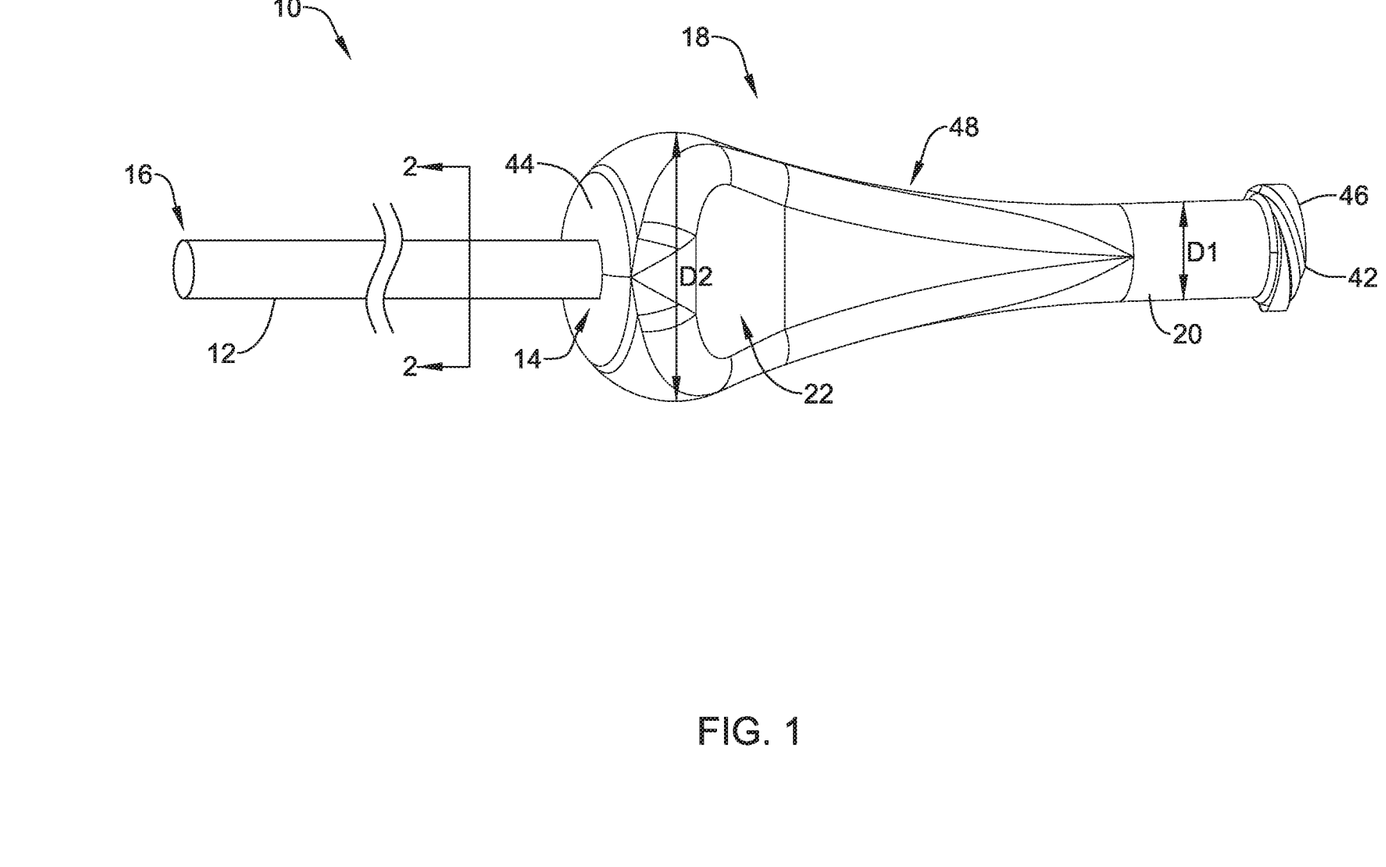
FIG. 1 is a plan view of an illustrative catheter and hub assembly.

FIG. 1 is a plan view of a catheter 10 in accordance with an embodiment of the present invention. The catheter 10 can be one of a variety of different catheters. In some cases, the catheter 10 may be an intravascular catheter. Examples of some intravascular catheters include microcatheters, drug delivery catheters, diagnostic catheters and guide catheters. FIG. 1 illustrates a microcatheter, but the invention is not limited to such. The intravascular catheter 10 can be manufactured using conventional techniques.

The catheter 10 can be sized in accordance with its intended use. For example, the catheter 10 can have a length that is in the range of about 50 to 200 centimeters and can have a diameter that is in the range of about 1.7 French (F), but can be as large as about 12 F for certain applications.

In the illustrated embodiment, the catheter 10 may include an elongate shaft 12 that has a proximal end 14 and a distal end 16. A hub assembly 18 can be connected to or disposed about the proximal end 14 of the elongate shaft 12. The hub assembly 18 may include a main body portion 20 and a gripping portion 22. The hub body 20 may extend from a proximal end 42 to a distal end 44. The proximal end 42 may include a Luer fitting 46, or other structure to facilitate connection to another medical device.

Some hub assemblies incorporate a strain relief on the proximal part of the shaft bonded to the hub, so as to provide a gradual stiffness transition from the rigid hub to the more flexible shaft. A sudden change in stiffness can be a location for kink and the gradual wall thickness change of the strain relief may provide a gradual change in stiffness of the assembly. However, an elastomeric strain relief may not be required when the shaft is kink-resistant. Some illustrative kink-resistant shafts may include reinforced shafts (e.g., braided, coiled, micro-machined, etc.). It is further contemplated that strain reliefs may not be needed when the reinforcement can provide kink resistance in the hub location, which may make additional strain relief redundant and/or irrelevant. Further when the shaft is much stiffer than the strain relief material, the strain relief may not have much effect on the assembly properties. Additionally, in the case of high pressure microcatheter, the strain relief may hide a potential leak and/or kink under it and/or may limit the design options for the distal end of the hub (as it has be designed to mate with the strain relief. In some cases, the hub assembly 18 of the catheter 10 may provide strain relief functionality such that a separate strain relief portion is not required.

The hub assembly 18 may be connected to the proximal end 14 of the elongate shaft 12, The hub assembly 18 may be secured to the catheter shaft 12 at the proximal end 14 of the shaft 12 using any suitable technique, for example, by adhesive, friction fitting, mechanically fitting, chemically bonding, thermally bonding, heat shrink materials, molding, casting, welding (e.g., resistance or laser welding), soldering, brazing, the use of an outer sleeve or polymer layer to bond or connect the components, or the like, or combinations thereof. In some embodiments, the distal end of the hub assembly 18 can be cast, molded or shaped onto the proximal end 14 of the shaft 12 such that it is connected to the proximal end 14. In other embodiments, the hub assembly 18 may be formed as a separate component and subsequently attached (e.g., adhered, press-fit, etc.) to the proximal end 14 of the catheter shaft 12.

The hub body 20 may be a generally flared tubular configuration which has a first diameter D1 adjacent or proximate to the proximal end 42, such as at a first location, and a second diameter D2 adjacent or proximate to the distal end 44, such as at a second location. The second diameter D2 may be larger than the first diameter D1. The hub body 20 may transition from the first diameter D1 to the second diameter D2 over an intermediate or transition region 48. The change from the first diameter D1 to the second diameter D2 may be a gradual or sloped change. In some cases, the transition may be abrupt or step-wise.

The gripping portion 22 may provide a region for the user to grip the hub assembly 18 while locking or unlocking any accessory or syringe to the Luer 46. The gripping portion 22 may be a generally smooth flat region in an otherwise rounded or curved body. The hub assembly 18 may include a second gripping portion 22 on the opposite side of the body 20. In addition to providing a gripping portion 22, the flat regions may also provide orientation reference points to a physician. It is further contemplated that the gripping portions 22 may be more ergonomic than a traditional hub with "wings". Syringe injection may be used to inject particulates, chemotherapy, contrast, etc. through the hub assembly 18 and into the catheter shaft 12. As microcatheter inner diameters are getting smaller and smaller, it may take more pressure to inject. A typical hub design (e.g., including wings) may hurts the user's hands as the distal end (e.g., wings) creates pressure points which may dig into a user's hand. The smooth, flat gripping portion 22 may provide a more ergonomic hub assembly 18 which may reduce pressure points.

Figure 2:
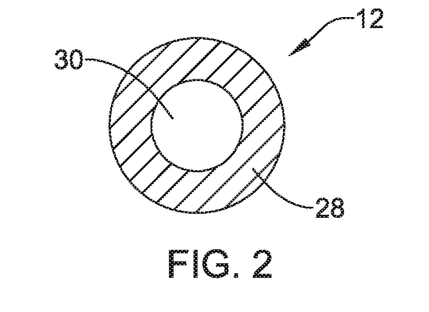
FIG. 2 is a cross-sectional view of the illustrative catheter of FIG. 1, taken at line 2-2.

FIG. 2 is a cross-sectional view of the elongate shaft 12, taken along line 2-2 of FIG. 1. A lumen 30 may extend through the elongate shaft 12 from the proximal end 14 to the distal end 16 thereof. In some embodiments, the elongate shaft 12 may be formed of a single polymer layer 28, which can be any suitable polymeric material, such as, but not limited to, a thermoplastic polymer material. The single polymer layer 28 can be extruded or otherwise formed from a single polymer or from a blend of polymers. The elongate shaft 12 can also include additional polymer layers.

Figure 3:
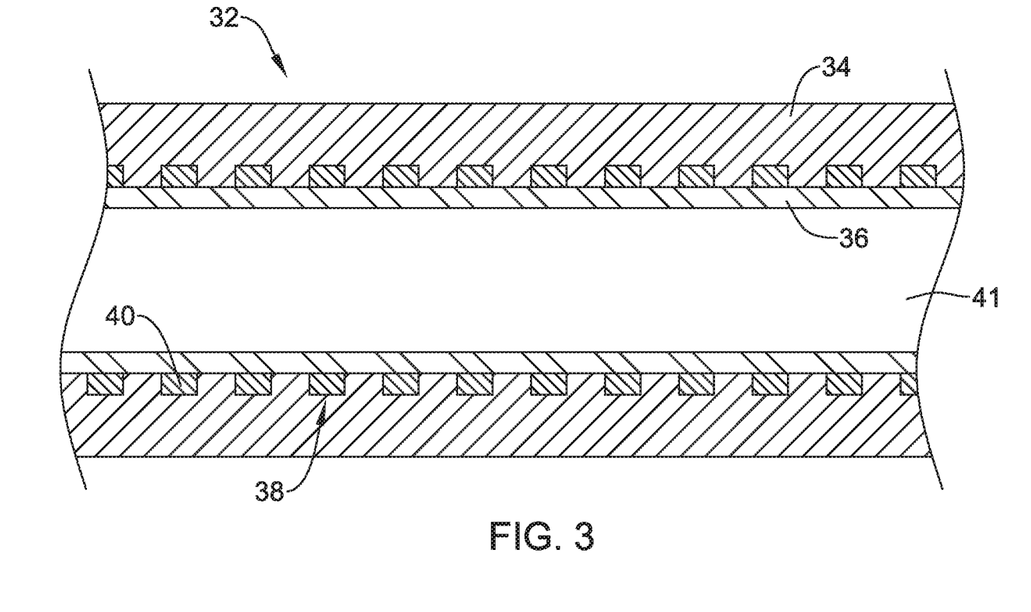
FIG. 3 is an illustrative cross-section of another illustrative catheter.

For example, FIG. 3 illustrates a cross-section of a portion of another exemplary elongate shaft 32 that may be used in place of or in combination with a single layer shaft (e.g., such as shaft 12). The elongate shaft 32 may include an outer polymer layer 34, an inner polymer layer 36, and an intermediate reinforcing layer 38. In some embodiments, the inner polymer layer 36 can be formed of or include a coating of a material having a suitably low coefficient of friction. Examples of suitable materials include polytetrafluoroethylene (PTFE), better known as TEFLON®. The inner layer 36 can be dimensioned to define a lumen 30 having an appropriate inner diameter to accommodate its intended use. In some embodiments, the inner layer 36 can define a lumen 41 having a diameter of in the range of 0.0160 inches (0.406 millimeters (mm)) to about 0.0170 inches (0.432 mm) or about 0.0165 inches (0.419 mm) and can have a wall thickness in the range of 0.0005 inches (0.0127 mm) to about 0.0015 inches (0.0381 mm), or about 0.001 inches (0.0254 mm). The lumen 41 may extend from a proximal end to a distal end of the elongate shaft 32.

The outer polymer layer 34 can be formed from any suitable polymer that will provide the desired strength, flexibility or other desired characteristics. Polymers with low durometer or hardness can provide increased flexibility, while polymers with high durometer or hardness can provide increased stiffness. In some embodiments, the polymer material used is a thermoplastic polymer material. Some examples of some suitable materials include polyurethane, elastomeric polyamides, block polyamide/ethers (such as PEBAX), silicones, and co-polymers. The outer layer 34 can be a single polymer, multiple longitudinal sections or layers, or a blend of polymers. By employing careful selection of materials and processing techniques, thermoplastic, solvent soluble, and thermosetting variants of these materials can be employed to achieve the desired results.

In some embodiments, a thermoplastic polymer such as a co-polyester thermoplastic elastomer, for example that available commercially under the ARNITEL® name, can be used. The outer layer 34 can have an inner diameter that is about equal to the outer diameter of the inner layer 36. The outer layer 34 can have an inner diameter that is slightly greater than the outer diameter of the inner layer 36 to accommodate the thickness of the reinforcing layer 38.

In some embodiments, the outer layer 34 of the shaft can have an inner diameter in the range of about 0.0165 inches (0.4191 mm) to about 0.153 inches (3.886 mm) and an outer diameter in the range of about 0.023 inches (0.584 mm) to about 0.159 inches (4.039 mm). Part or all of the outer layer 34 can include materials added to increase the radiopacity of the outer layer 34, such as 50% bismuth subcarbonate.

In some embodiments, a reinforcing layer 38 can be positioned between the inner layer 36 and the outer layer 34. A reinforcing braid layer 38 can be formed using a variety of different weave patterns, such as a three-over-three, a four-over-four, and the like. In some embodiments, in order to minimize impact on catheter diameter, the reinforcing layer 38 can be formed from braid wires or a single ribbon 40 or multiple ribbons that are helically wrapped around the inner layer 36.

The braid wires or ribbon 40 can have a rectangular, round, oval or other cross-sectional shape. In some embodiments, the braid wires or ribbon 40 can have a flat cross section such that it has a width that is at least about twice its height. The braid wires or ribbon 40 can be formed of any suitable material, such as stainless steel, tungsten, gold, titanium, silver, copper, platinum or iridium. The braid wires or ribbon 40 can also be formed from non-metallic material such as KEVLAR® (poly paraphenylene terephthalamide) fibers, LCP (liquid crystal polymer) fibers, or glass fibers and combinations thereof.

Figure 4:
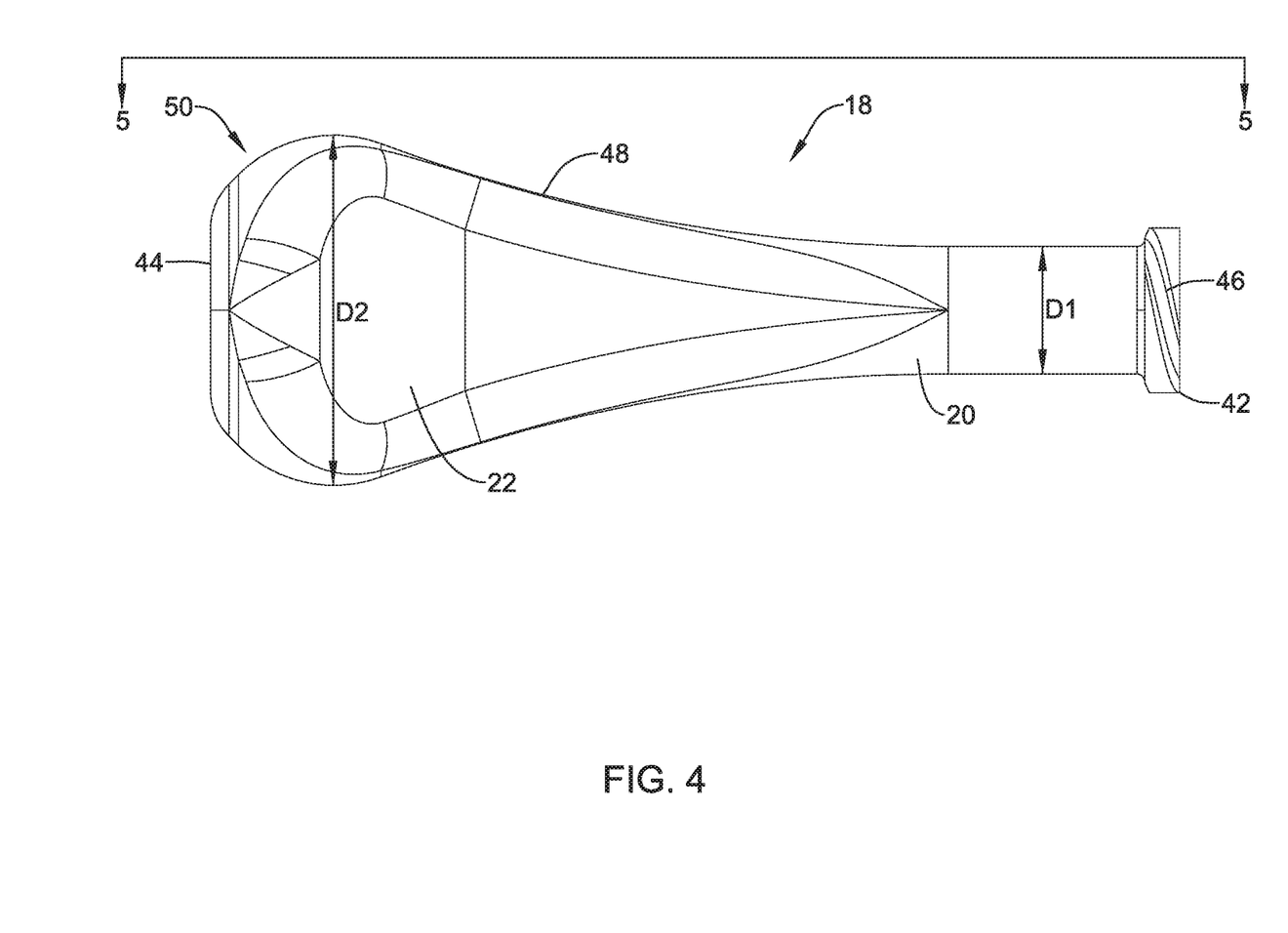
FIG. 4 is a side view of the illustrative hub of FIG. 1.

FIG. 4 is a side view of the hub assembly 18. The hub body 20 may be made of a polymeric material such as, but not limited to, a polycarbonate material, or the like, that could be molded or cast. In some cases, the hub body 20 may be transparent which may aid in the bonding process (if so required) and/or facilitate the detection of internal failure modes. The distal end 44 of the hub body 20 may include a rounded or radiused surface 50. The rounded surface 50 may limit the radius that an elongate shaft can be bent, as described herein.

Figure 5:
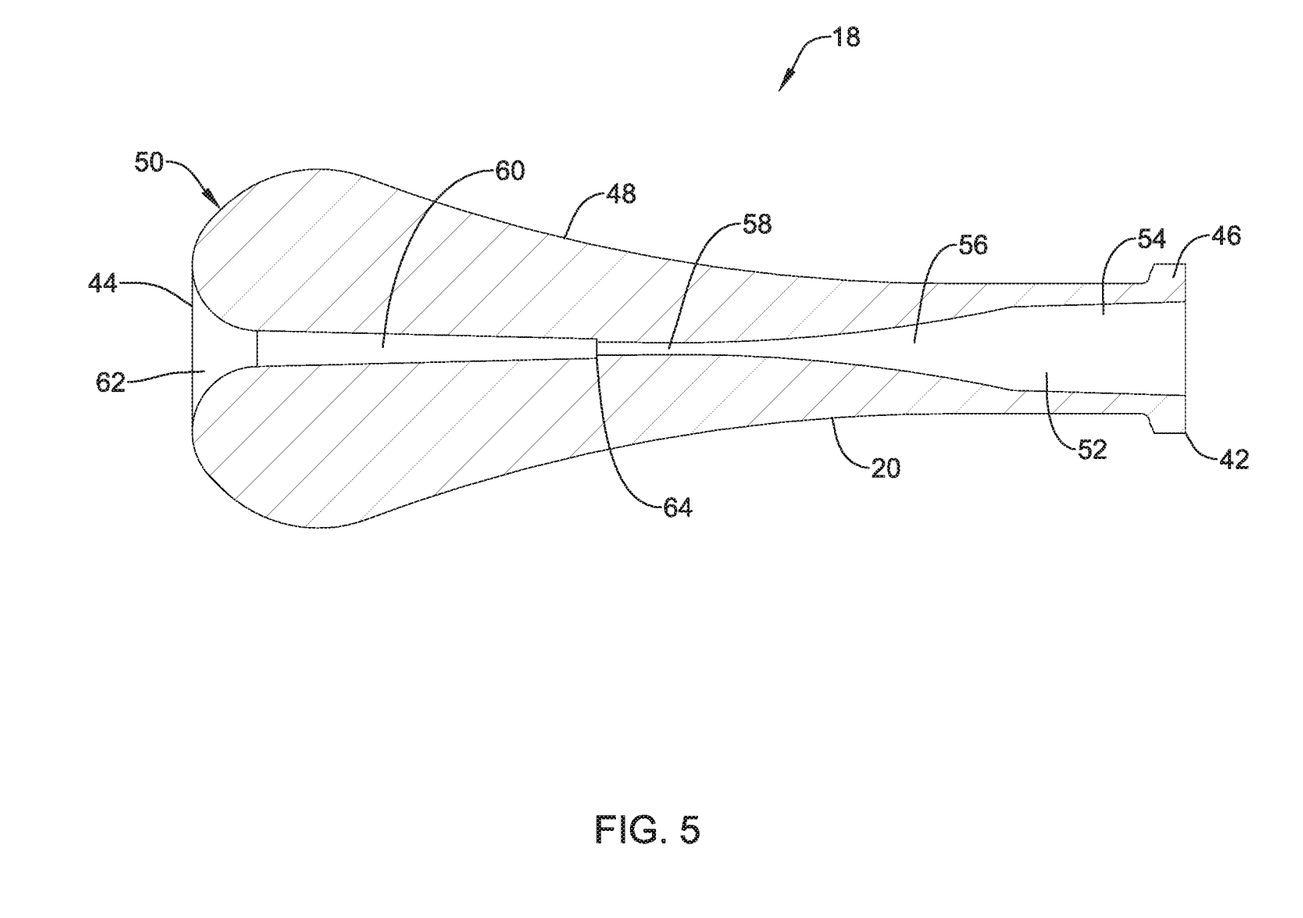
FIG. 5 is a cross-sectional view of the illustrative hub of FIG. 4, taken at line 5-5.

FIG. 5 is a cross-sectional view of the hub assembly 18, taken at line 5-5 of FIG. 4. The hub body 20 may include a lumen 52 extending from the proximal end 42 to the distal end 44. The lumen 52 may vary in diameter along the length thereof. In one illustrative embodiment, the lumen 52 may have a first region or proximal region 54 adjacent the proximal end 42. The first region 54 may be sized to receive a medical device, such as, but not limited to, a syringe. Distally adjacent to the first region 54 may be a first intermediate region 56 which may be tapered or sloped. The sloped first intermediate region 56 may decrease in diameter from a proximal end thereof to a distal end thereof. The sloped first intermediate region 56 may be configured to direct an injected fluid towards a smaller diameter second intermediate region 58. The smaller diameter intermediate region 58 may be similar in size and shape to a lumen of the catheter shaft, such as the lumen 30, 41 of the catheter shaft 12 described herein. The lumen 52 may further include a flared distal region 60 adjacent to the smaller diameter intermediate region 58. The flared distal region 60 may increase in diameter from the proximal end thereof to the distal portion 62 thereof. The distal end portion 62 of the lumen 52 may form a portion of the rounded surface 50 of the hub body 20.

The flared region 60 may be configured to receive a proximal portion of a catheter shaft. In some cases, the gradual flare may function as a strain relief as well as facilitate assembly by making it easier to bond the catheter shaft to the hub body 20. In some cases, the flared region 60 may also facilitate a press-fit assembly process. The lumen 52 may include a stop mechanism 64, such as, but not limited to, a step change in the diameter of the lumen 52, configured to limit proximal insertion of the catheter shaft, although this is not required. The described configuration of the lumen 52 is not intended to be limiting. The lumen 52 may have different configurations, as desired. For example, some regions that are shown as flared or tapered may be constant diameter regions and some regions that are shown as having constant diameter may be flared or tapered. Further the transition between regions may occur at any point along the length of the lumen 52, as desired.

Figure 6:
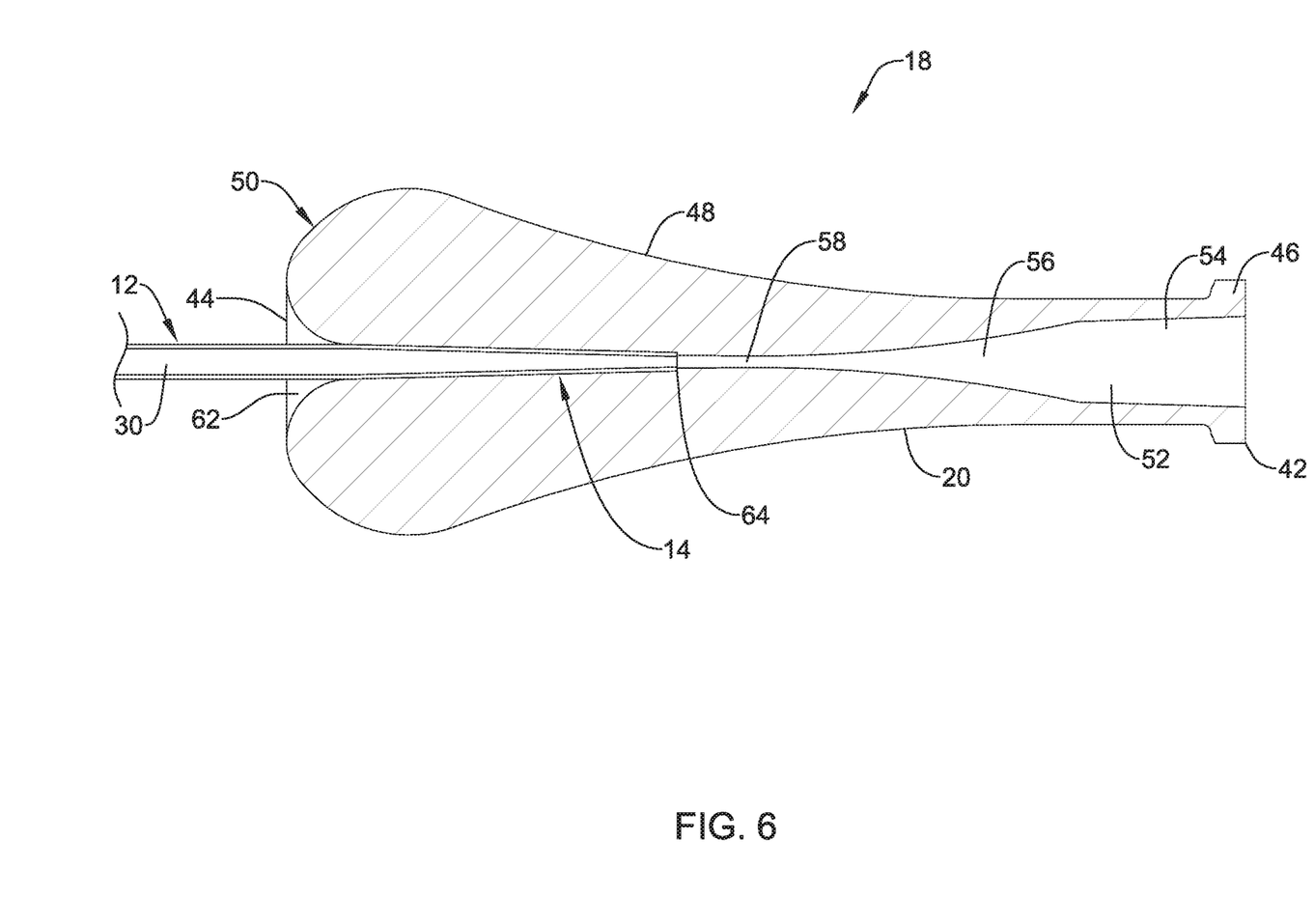
FIG. 6 is a cross-sectional view of a portion of the illustrative catheter of FIG. 1 in a first configuration.
Figure 7:
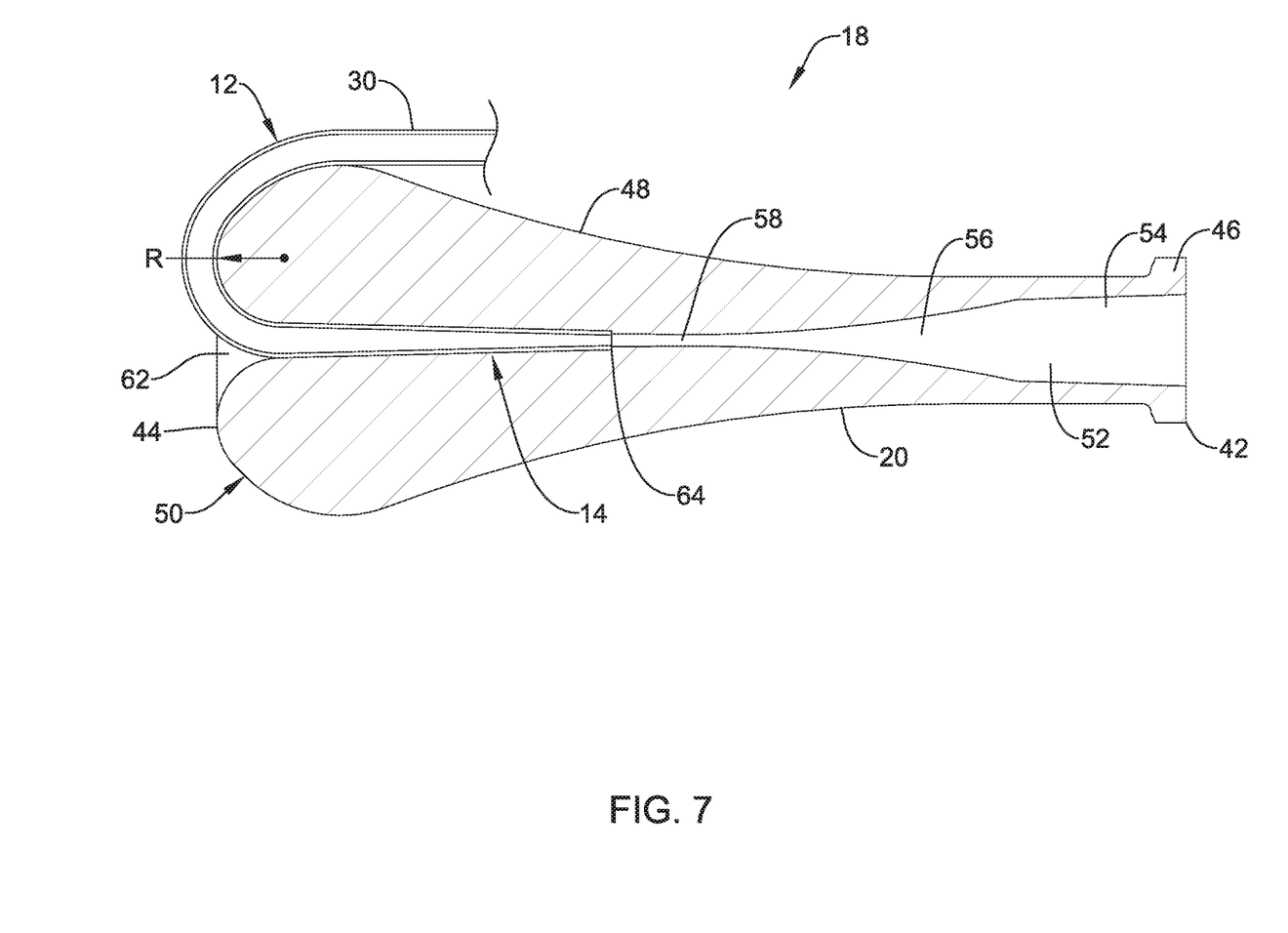
FIG. 7 is another configuration of the system of FIG. 6.

FIG. 6 is a cross-sectional view of the hub assembly 18 taken at line 5-5 in FIG. 4 including the elongate shaft 12. As can be seen, the proximal end 14 of the elongate shaft 12 may be disposed within the lumen 52 of the hub body 20. FIG. 7 is the cross-sectional view of the hub assembly 18 taken at line 5-5 in FIG. 4 including the elongate shaft 12 bent around the distal end 44 of the hub. The distal portion 62 of the lumen 52 and rounded surface 50 may be sized and shaped to limit the radius of bending of the elongate shaft 12. Some microcatheters may be designed to withstand a 3 millimeter bend (e.g., radius of curvature) without kinking at a centerline (e.g., longitudinal axis) of the elongate shaft 12 adjacent the proximal end thereof. In some cases, the distal end 16 may be designed to withstand a 2 millimeter bend (e.g., radius of curvature) without kinking at a centerline (e.g., longitudinal axis) of the elongate shaft 12. The outer surface (oriented in the direction of the bend) of the elongate shaft 12 may have a smaller radius of curvature R than the radius of curvature at the centerline when the elongate shaft 12 is bent, as can be seen in FIG. 7. Thus, the distal portion of the lumen 52 and the rounded portion may have a radius of curvature R that limits the bend of the elongate shaft 12 to 1 mm or less, greater than 1 mm, greater than 2 mm, greater than 3 mm, greater than 4 mm, greater than 5 mm, etc. It is contemplated that the radius of curvature R may be varied based on the structure of the elongate shaft 12. While the radius of curvature R is generally illustrated as constant, the radius of curvature R may vary over the rounded surface 50. In some cases, the distal portion 62 of the lumen 52 and the rounded surface 50 may have multiple radii and/or segments of curved (radiused) and line segments arranged to function as a non-kinking support. Other embodiments may include a generally elliptical rounded surface 50. The distal portion 62 of the lumen 52 and the rounded surface 50 may provide a support with a gradual curve which reduces or eliminates kinking of the elongate shaft 12. It is contemplated that the entire distal end 44 of the hub body 20 may be rounded in order to provide kink resistance regardless of which direction the elongate shaft 12 is moved. The hub body 20 may gradually transition from the rounded surface 50 to the flattened gripping region 22.

The materials that can be used for the various components of the medical devices and/or systems 10, 12, 18, (and/or other systems disclosed herein) and the various elements thereof disclosed herein may include those commonly associated with medical devices. For simplicity purposes, the following discussion makes reference to the catheter 10. However, this is not intended to limit the devices and methods described herein, as the discussion may be applied to other elements, members, components, or devices disclosed herein, such as, but not limited to, the elongate shaft 12 and the hub assembly 18, and/or elements or components thereof.

In some embodiments, the catheter 10, and/or components thereof, may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of catheter 10, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device system 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device system 10 to achieve the same result.

In some embodiments, a degree of Magnetic Resonance Imaging (MRI) compatibility is imparted into the medical device system 10. For example, catheter 10, and/or components or portions thereof, may be made of a material that does not substantially distort the image and create substantial artifacts (e.g., gaps in the image). Certain ferromagnetic materials, for example, may not be suitable because they may create artifacts in an MRI image. The catheter 10, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, an exterior surface of the medical device system 10 (including, for example, an exterior surface of the delivery system) may be sandblasted, bead-blasted, sodium bicarbonate-blasted, electropolished, etc. In these as well as in some other embodiments, a coating, for example a lubricious, a hydrophilic, a protective, or other type of coating may be applied over portions or all of the outer sheath, or in embodiments without an outer sheath over portions of the delivery system, or other portions of the medical device system 10. Hydrophobic coatings such as fluoropolymers provide a dry lubricity which improves device handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A hub assembly comprising:
   an elongate shaft having a proximal end, a distal end, and a lumen extending therebetween;
   a hub body having a proximal end region and a distal end region, the distal end region of the hub body affixed to the proximal end of the elongate shaft; and
   a second lumen extending from the proximal end region to the distal end region of the hub body, the second lumen of the hub body including a proximal region, an intermediate region, and a distal region, the distal region increasing in diameter from a proximal end of the distal region of the second lumen to a distal end of the hub body;
   wherein an entirety of the distal end of the hub body has a symmetrically rounded surface, the distal end of the hub body distal to the proximal end of the elongate shaft and the rounded surface configured to limit a radius of bending of the elongate shaft when the elongate shaft is bent relative to the hub body and having a radius of curvature of greater than 1 millimeter.

2. The hub assembly of claim 1, further comprising at least one gripping portion formed in a side surface of the hub body.

3. The hub assembly of claim 2, wherein the at least one gripping portion comprises a generally flat region.

4. The hub assembly of claim 3, wherein the rounded surface gradually transitions to the generally flat region.

5. The hub assembly of claim 2, wherein the at least one gripping portion comprises two gripping portions, each positioned on an opposing side of the hub body.

6. The hub assembly of claim 1, wherein the second lumen has a step-wise change in diameter at the proximal end of the distal region.

7. The hub assembly of claim 1, wherein the rounded surface extends into the second lumen.

8. The hub assembly of claim 1, wherein the proximal region of the second lumen comprises a tapered region that is configured to direct a fluid distally from a larger diameter to a smaller diameter region.

9. The hub assembly of claim 1, wherein the hub body comprises a polycarbonate.

10. The hub assembly of claim 1, wherein the hub body is transparent.

11. A hub assembly comprising:
    an elongate shaft having a proximal end, a distal end, and a lumen extending therebetween;
    a generally tubular hub body increasing in outer diameter from a proximal end region to a distal end region thereof, the distal end region of the hub body affixed to the proximal end of the elongate shaft;
    a second lumen extending from the proximal end region to the distal end region of the hub body; and
    at least one generally flat surface formed in a first side surface of the generally tubular body to form at least one gripping portion;
    wherein an entirety of the distal end region of the hub body forms a convex rounded surface extending continuously about a circumference thereof, the entirety of the convex rounded surface limiting a radius of bending of the elongate shaft to reduce or prevent kinking of the elongate shaft when the elongate shaft follows the convex rounded surface and having a radius of curvature of greater than 1 millimeter.

12. The hub assembly of claim 11, wherein the convex rounded surface gradually transitions to the generally flat region.

13. The hub assembly of claim 11, wherein a distal region of the second lumen comprises a flared region that increases in diameter from a first location at least proximate the proximal end region of the hub body to the distal end region of the hub body.

14. The hub assembly of claim 11, wherein the convex rounded surface extends into the second lumen.

15. A microcatheter, comprising:
    an elongate shaft having a proximal end, a distal end, and a lumen extending therebetween;
    a hub assembly having a proximal end region and a distal end region, the distal end region of the hub assembly affixed to the proximal end of the elongate shaft, the hub assembly comprising:
    a generally tubular hub body increasing in outer diameter from the proximal end region to the distal end region, wherein the outer diameter reaches a maximum outer diameter closer to the distal end region than the proximal end region or in the distal end region;
    a second lumen extending from the proximal end region to the distal end region of the hub body, wherein a distal portion of the lumen increases in diameter in a distal direction; and at least one gripping portion formed in a first side surface of the generally tubular hub body;

wherein the distal end region of the hub body has a rounded surface, the rounded surface configured to limit a radius of bending of the elongate shaft when the elongate shaft is bent relative to the hub body and having a radius of curvature of greater than 1 millimeter.

16. The microcatheter of claim 15, wherein the hub assembly is molded over the proximal end of the elongate shaft.

17. The microcatheter of claim 15, wherein the proximal end of the elongate shaft is press fit into the second lumen of the hub assembly.

18. The microcatheter of claim 15, wherein the proximal end of the elongate shaft is secured within the second lumen of the hub assembly with an adhesive.

* * * * *